(12) United States Patent
Larsson et al.

(10) Patent No.: US 8,469,937 B2
(45) Date of Patent: Jun. 25, 2013

(54) METHOD OF MANUFACTURING ABSORBENT ARTICLES CONTAINING ELASTICS

(75) Inventors: Gunnar Larsson, Göteborg (SE); Carin Håkansson, Billdal (SE); Kent Hermansson, Västra Frölunda (SE); Roy Hansson, Mölndal (SE)

(73) Assignee: SCA Hygiene Products AB, Goteborg (SE)

( * ) Notice: Subject to any disclaimer, the term of this patent is extended or adjusted under 35 U.S.C. 154(b) by 751 days.

(21) Appl. No.: 12/666,914

(22) PCT Filed: Jul. 5, 2007

(86) PCT No.: PCT/SE2007/050501
§ 371 (c)(1),
(2), (4) Date: Dec. 28, 2009

(87) PCT Pub. No.: WO2009/005432
PCT Pub. Date: Jan. 8, 2009

(65) Prior Publication Data
US 2011/0022018 A1    Jan. 27, 2011

(51) Int. Cl.
*A61F 13/15*    (2006.01)
(52) U.S. Cl.
USPC .................................. 604/385.24; 156/161
(58) Field of Classification Search
USPC .................................. 156/161, 163, 164, 229
See application file for complete search history.

(56) References Cited

U.S. PATENT DOCUMENTS

| 4,578,133 | A | 3/1986 | Oshefsky et al. |
| 4,626,305 | A | 12/1986 | Suzuki et al. |
| 4,687,477 | A | 8/1987 | Suzuki et al. |
| 4,762,582 | A * | 8/1988 | de Jonckheere .............. 156/164 |

(Continued)

FOREIGN PATENT DOCUMENTS

| CN | 1302593 | 7/2001 |
| CN | 1479601 A | 3/2004 |

(Continued)

OTHER PUBLICATIONS

Office Action (Decision on Grant) dated Mar. 14, 2011, issued in the corresponding Russian Patent Application No. 2010103779, and an English Translation thereof.

(Continued)

*Primary Examiner* — Lynne Anderson
*Assistant Examiner* — Bradley Philips
(74) *Attorney, Agent, or Firm* — Buchanan Ingersoll & Rooney PC

(57) ABSTRACT

A method of manufacturing absorbent articles having an absorbent core (18,20,22) enclosed between casing sheets (16,24) and elastic elements (26-28) located in a front part and/or rear part of the article, includes the steps of laying a row of absorbent cores (18,20,22) on a first web (16) of casing material running in a machine direction with the longitudinal direction of the cores being extended in the machine direction, applying a second web (24) of casing material onto the web containing the row of absorbent cores, applying elastic elements (26-28) to one of the webs before it contacts the row of absorbent cores, thereby forming a row of connected absorbent article blanks, and thereafter cutting individual absorbent articles out of the row of article blanks.

10 Claims, 4 Drawing Sheets

U.S. PATENT DOCUMENTS

| | | | |
|---|---|---|---|
| 4,850,989 A | | 7/1989 | Villez |
| 4,992,125 A | | 2/1991 | Suzuki et al. |
| 4,995,928 A | | 2/1991 | Sabee |
| 5,275,676 A | * | 1/1994 | Rooyakkers et al. ......... 156/164 |
| 5,413,654 A | * | 5/1995 | Igaue et al. ................... 156/161 |
| 6,068,435 A | | 5/2000 | Börjesson |
| 6,250,357 B1 | | 6/2001 | Niedermeyer |
| 6,464,678 B2 | | 10/2002 | Shimoe et al. |
| 6,569,275 B1 | | 5/2003 | Popp et al. |
| 6,808,582 B2 | | 10/2004 | Popp et al. |

FOREIGN PATENT DOCUMENTS

| | | |
|---|---|---|
| EP | 0 236 032 | 9/1987 |
| EP | 1 114 631 | 7/2001 |
| GB | 2 118 021 A | 10/1983 |
| WO | WO 98/44882 A1 | 10/1998 |
| WO | WO 02/13742 | 2/2002 |
| WO | WO 02/45637 A1 | 6/2002 |

OTHER PUBLICATIONS

International Search Report of Application No. PCT/SE2007/050501 dated Apr. 1, 2008.

Written Opinion of the International Searching Authority of Application No. PCT/SE2007/050501 dated Apr. 1, 2008.

Written Opinion of the International Preliminary Examining Authority of Application No. PCT/SE2007/050501 dated Jul. 23, 2009.

Office Action (Notification of the First Office Action) dated Apr. 26, 2012, issued in corresponding Chinese Patent Application No. 200780053578.1, and an English Translation thereof. (3 pages).

Office Action issued in corresponding Chinese Patent Application No. 200780053578.1, dated Feb. 18, 2013 and English translation.

* cited by examiner

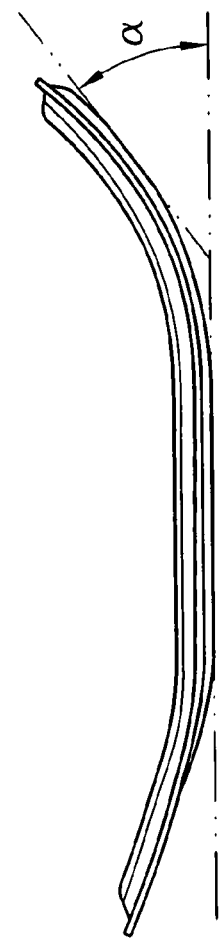
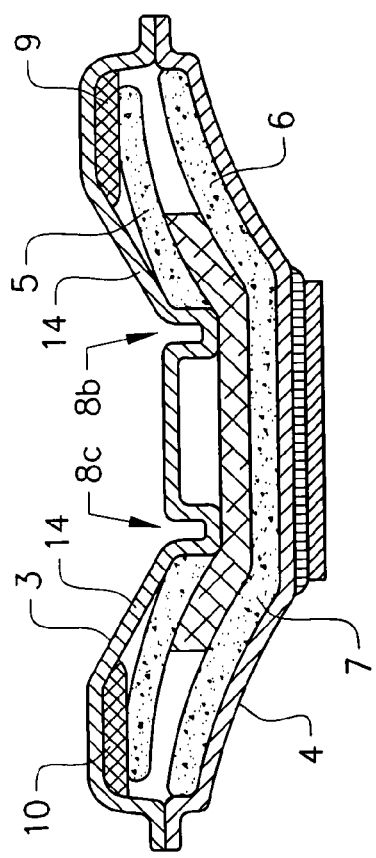
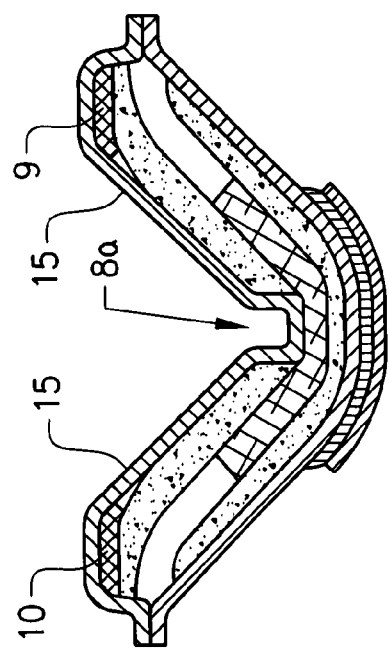

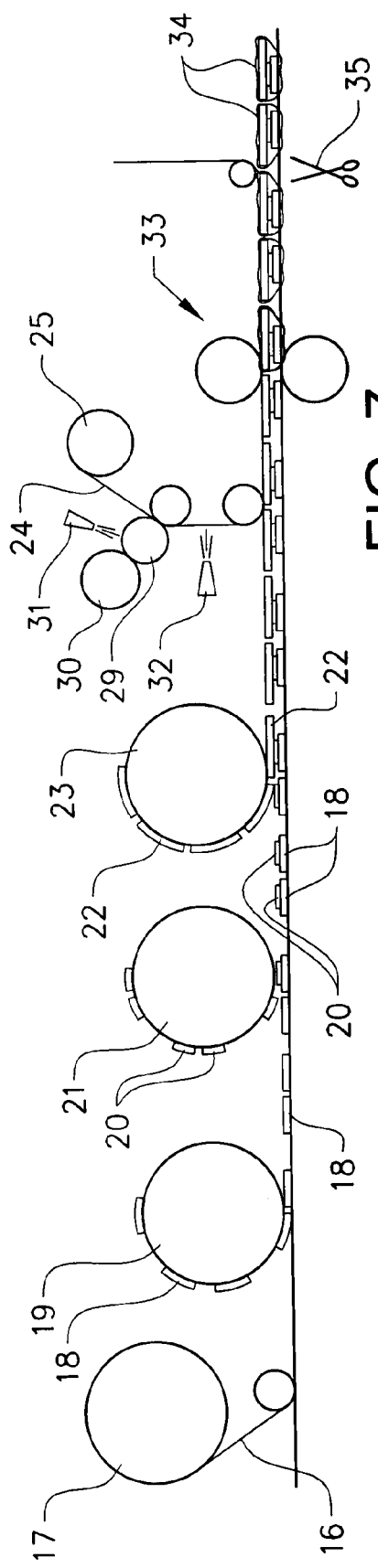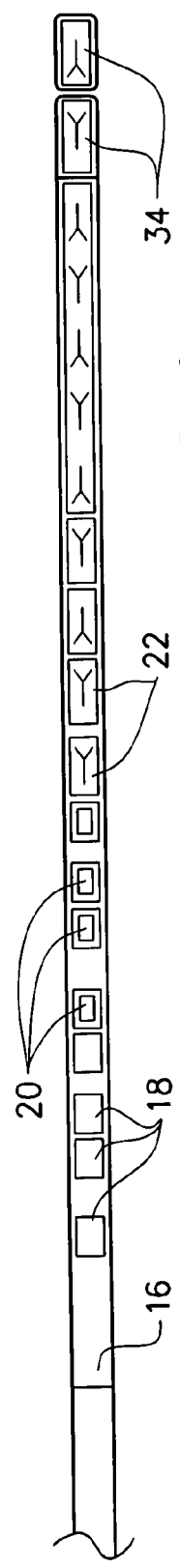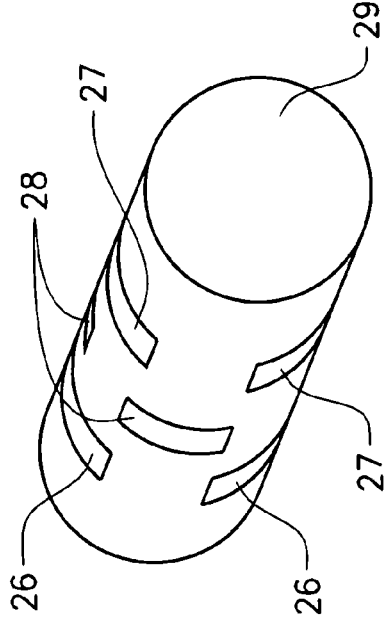

METHOD OF MANUFACTURING ABSORBENT ARTICLES CONTAINING ELASTICS

TECHNICAL FIELD

The invention relates to a method of manufacturing absorbent articles having an absorbent core enclosed between casing sheets and elastic elements located in a front part and/or rear part of the article, comprising the steps of laying a row of absorbent cores on a first web of casing material running in a machine direction with the longitudinal direction of the cores being extended in the machine direction, applying a second web of casing material onto the web containing the row of absorbent cores, applying elastic elements to one of said webs before it contacts said row of absorbent cores, thereby forming a row of connected absorbent article blanks, and thereafter cutting individual absorbent articles out of the row of article blanks. The invention also relates to an article produced by this method.

BACKGROUND OF THE INVENTION

Pre-tensioned elastics are often provided to sanitary absorbent articles, such as incontinence protectors, diapers, sanitary napkins or the like, in order to enable the article to obtain and maintain a desired three-dimensional shape when the pre-tensioned elastics are allowed to retract after manufacture. The elastics do not usually extend along the whole length of the articles so in continuous in-line production of absorbent articles, the elastics are at intervals laid onto and are attached to a web of casing material. It is of course important that the positioning of the elastics is accurate so that the elastics will be placed in correct position in the produced articles. The laying-out of pre-tensioned elastics at intervals on a web in the production line can be troublesome and does reduce the production efficiency, especially the synchronization between the laying-out device, the cutter of the elastics and the web can create problems.

The objective of the present invention is to simplify the laying-out of elastics in a method of manufacturing absorbent articles, such as incontinence protectors, sanitary napkins, diapers and the like.

SUMMARY OF THE INVENTION

This objective is obtained by a method of manufacturing absorbent articles having an absorbent core enclosed between casing sheets and elastic elements located in a front part and/or rear part of the article, comprising the steps of laying a row of absorbent cores on a first web of casing material running in a machine direction with the longitudinal direction of the cores being extended in the machine direction, applying a second web of casing material onto the web containing the row of absorbent cores, applying elastic elements to one of said webs before it contacts said row of absorbent cores, thereby forming a row of connected absorbent article blanks, and thereafter cutting individual absorbent articles out of the row of article blanks, characterised in that the absorbent cores are laid onto the first web front part to front part and rear part to rear part and continuous elastic elements are applied over two subsequent absorbent cores with a length in the longitudinal direction corresponding to twice the length of the respective elastic element in the front and/or rear part of the article and a possible distance between adjacent article blanks in the row of article blanks.

In such a method the cutting device cutting out individual articles from the row of connected article blanks is used also to make the final cut of the elastic elements. Moreover, all elastic elements and the adhesive used for attachment thereof can be laid in twice as long sequences than if separate elastic elements should be laid-out and attached for every individual article. Since intermittent process steps often requires a stop/start of a conveyer in the production line, one "gains time" for the different process steps and the production tolerances becomes smaller or can be maintained at a higher production rate, when the number of stop/starts are decreased.

In a first preferred embodiment said first web of casing material is a web of backing sheet material and said elastic elements are applied to the second web of casing material, said second web of casing material is a web of top sheet material.

In a second preferred embodiment said second web of casing material is a web of backing sheet material and said elastic elements are applied to the first web of casing material, said first web of casing material is a web of top sheet material.

Preferably, elastic elements are applied to the web of top sheet material in positions corresponding to opposite lateral sides of the front part of each absorbent core. An elastic element is preferably also applied to the web of top sheet material in a position corresponding to the rear part of each absorbent core and is extended along the longitudinal axis of said web. By the placement of the absorbent cores with their front ends and rear ends turned against each other, the risk that a piece of an elastic element disposed in the rear part of the article blank by mistake will reach into the front part of an adjacent article blank in the connected row of article blanks.

Advantageously, each elastic element has a straight extension. Thereby the laying-out of elastic elements can be made faster than if the elastic elements are curved. Furthermore, said elastic elements will not influence said row of connected article blanks with elastic forces directed in a cross direction.

The elastic elements are preferably attached to lateral side portions of the absorbent cores.

The invention also relates to an absorbent article manufactured by the method described above and having an absorbent core enclosed between casing sheets and elastic elements located in a front part and/or rear part of the article, characterised in that the elastic elements in the front part of the article extend to the limit of the front end of the article.

In a preferred embodiment, the elastic elements in the front part of the article are attached to opposite lateral side portions of the absorbent core.

An elastic element can also extend along the longitudinal symmetry axis in the rear portion of the article.

BRIEF DESCRIPTION OF THE DRAWINGS

The invention will now be described with reference to the enclosed Figures, of which;

FIG. 4 is a sectional view along line IV-IV in FIG. 3, FIG. 5 is a sectional view along line V-V in FIG. 3, FIG. 6 is a schematic side view of the article in FIG. 3, FIG. 7 schematically, in a side view, discloses a production line for manufacturing absorbent articles according to a preferred embodiment of the method, FIG. 8 schematically discloses a plan view of the production line in FIG. 1, FIG. 9 schematically discloses an element of a device for laying-out elastic elements, and FIG. 10 schematically discloses a continuous web of waste material.

DESCRIPTION OF EMBODIMENTS

Figure 2:
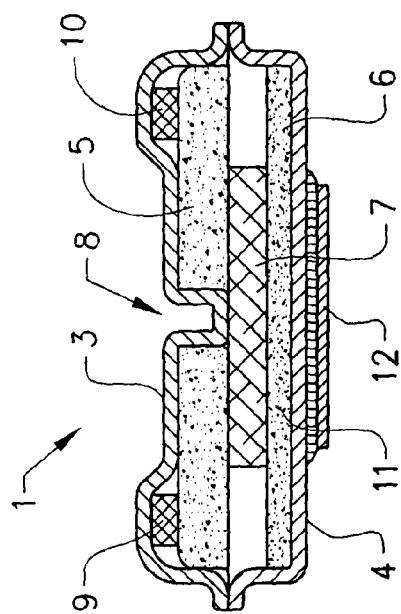
FIG. 2 is a sectional view along line II-II in FIG. 1, FIG. 3 schematically shows a perspective view of the absorbent article in FIG. 1 with the elastic elements in a contracted state.
Figure 1:
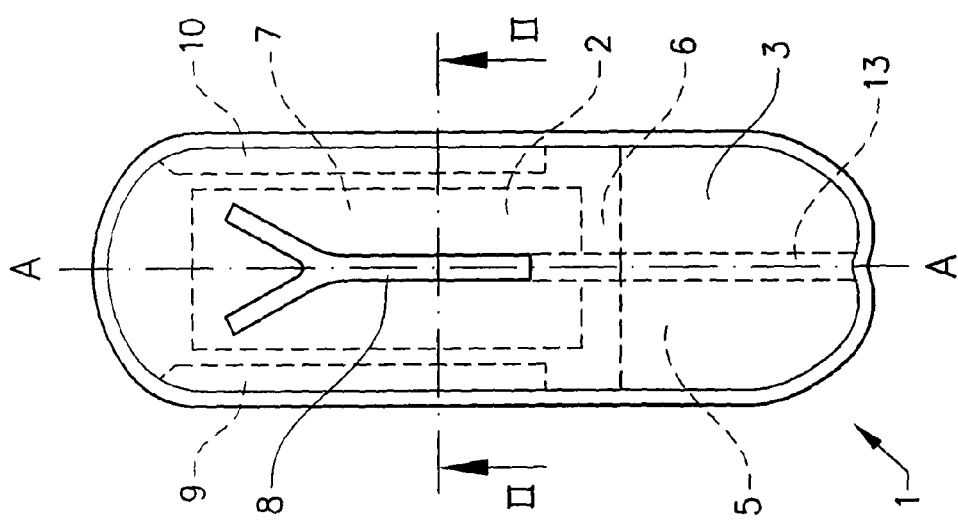
FIG. 1 schematically shows a plan view of an absorbent article manufactured according to a preferred embodiment of the method, the article shown in planar state, i.e. all elastic elements are stretched.

FIGS. 1 and 2 disclose an absorbent article 1 in form of a protector for light incontinent females in a planar state, i.e. the state such articles are held in during manufacturing thereof. The article 1 is composed of an absorbent body or core 2 enclosed between a top sheet 3 and a backing sheet 4. The top sheet 3 and backing sheet 4 extend beyond the absorbent core 2 around its whole circumference and are attached to each other in the portions extending beyond the core.

The absorbent core 2 consists of three layers; an upper absorbent layer 5 being proximal to the top sheet, a lower absorbent layer 6 being distal to the top sheet and an acquisition layer 7 disposed between the upper and lower absorbent layers. A through-going hole 8 having Y-shape is made in the upper absorbent layer 5. The central leg of said Y is extended along the longitudinal axis A-A of the article and the legs of said Y diverging from said central leg are closer to the front end of the article, i.e. the upper end in FIG. 1, than the central leg. The major part of hole 8 is disposed in the front half of the article 1.

Two elastic bands 9 and 10 are attached in a pre-tensioned state to opposite longitudinal edges of upper absorbent layer and extend along said hole 8 parallel to the longitudinal axis A-A. These elastic bands extend beyond the hole 8 in the longitudinal direction, at least in the front portion of the article in which the elastic bands 9,10 extend to the limit of the front end edge of the article 1. The top sheet 3 is attached to these elastic bands 9,10 and also to the bottom of hole 8, i.e. to the upper side of the acquisition layer 7.

The article 1 also comprises a layer of adhesive 11 for releasably attaching the article to the inside of a pair of underpants and a release layer 12 protecting the adhesive layer before use.

The article 1 also comprises a third elastic band 13 extending along the longitudinal axis A-A from the rear end portion of hole 8 to the limit of the rear end of the article.

The acquisition layer 7 extends beyond the hole 8 both in a longitudinal direction and in a lateral direction. The lower absorbent layer 6 has a greater extension than the acquisition layer both in a longitudinal and lateral direction but is shorter than the upper absorbent layer 5 in the longitudinal direction so that the upper absorbent layer 5 is the only layer of the absorbent core in a rear end portion of the absorbent core.

Figure 3:
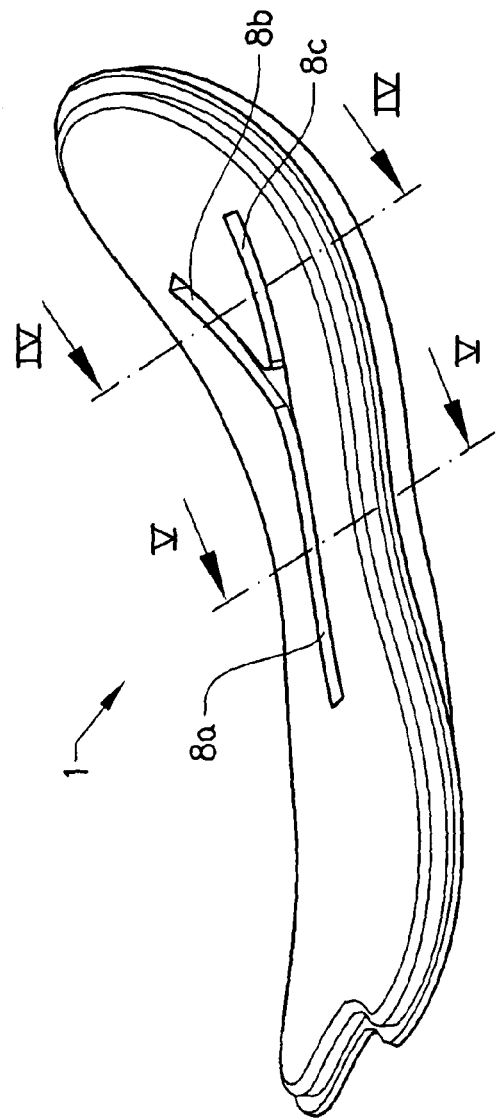

FIG. 3 is a schematic perspective view of the article 1 after that the pre-tensioned elastic bands 9, 10 and 13 have been allowed to contract after manufacture of the article. As is evident from FIG. 3, the forward part of the article has been raised above the remaining part thereof due to the contraction, i.e. the shortening, of the elastic bands 9 and 10. Moreover, the portions of the absorbent core disposed laterally of the hole 8 have been folded up, the channels 8a,8b and 8c in the upper absorbent layer formed by hole 8 functioning as folding lines. Thereby, a bowl shape is formed both in the front portion of the article containing channels 8b and 8c and the middle portion containing channel 8a. In the front portion, a triangular substantially flat part, see FIG. 4, is present in the region between the diverging legs 8b and 8c of the Y-shaped hole 8 and forms the bottom of bowl. The parts of the front portion of the absorbent core disposed laterally of legs or channels 8b and 8c constitute walls 14 of the bowl in the front portion. These parts have a triangular configuration with their apices directed forward, i.e. in the opposite direction as the apex of the bottom of the bowl. In the middle portion, see FIG. 5, the bowl shaped has the form of a valley. The walls 15 in the valley-shaped bowl in the middle portion of the article have a larger height than the walls 14 in the front part of the front portion of the article and consequently the article is wider in this front portion than in the middle portion. Behind the rear end of the channel 8a in the middle portion the height of the walls 15 will rapidly decrease so that the rear portion of the article will essentially be planar. In the middle portion of the article containing the channel 8a, the article will thus be narrower than in both the front and rear portion thereof as is schematically indicated in FIG. 3.

In the rear end portion of the article 1, the contraction of the elastic band 13 gives the end part a slightly upwardly curved configuration.

In FIG. 6 a side view of the article 1 according to FIG. 3 is shown. As is evident from this Figure most of the curving of the absorbent core in the longitudinal direction due to the contraction of elastic bands 9,10 occur in a region located longitudinally around the point where the three legs of hole 8 meet. The region containing the bottom of the bowl formed in the front portion will remain substantially planar as well as the region containing the central leg 8a of the hole 8. When the latter region is placed on a horizontal plane, as in FIG. 6, an angle $\alpha$ can be defined between the above mentioned two regions along the longitudinal symmetry line thereof. The value of this angle will be dependent on the contractive forces of the pre-tensioned elastic bands 9, 10. In the sense of the present invention, the contractive forces shall be so strong that the angle $\alpha$ is greater than 30 degrees.

Incontinence protectors, sanitary napkins and the like articles are usually packaged in a folded and planar state. In known articles of this kind with elastic elements provided outside of the absorbent core, the user must usually manually create the bowl form of the article which then is maintained by the elastics. When article 1 is taken out of a package it assumes by itself the configuration schematically disclosed in FIGS. 3-6 and the article is thus ready for application directly after being taken out of its package. Furthermore, the configuration of article 1 is very well adapted to the female body and the curvature of the article also indicates clearly to the user where the article should be located in relation to the body. The greater width of the article in the front portion contributes to hold an applied article in place so that it does not slide rearwards due to movements of the user.

The placement and attachment of the elastic bands onto the absorbent core will hold the core closer to the body of the user compared with similar articles having elastic elements located outside the absorbent core. Moreover, the attachment of the top sheet 3 to the bottom of hole 8 prevents the top sheet from leaving the surface of the absorbent core during folding up of the walls of the bowls. The top sheet material in the centre, the wetting area, will thus be held away from the body of the user in the bowl formed in the front and middle portions so that the risk for having a wet surface abutting the body of the user is reduced.

In the applied state of article 1, the elastic band 13 will contribute to hold the rear portion of the article against the body of the user between the buttocks of the user. In the portion of the article which in use is to be disposed between the buttocks of the user, the absorbent core only contains the upper absorbent layer. The absorbent core can therefore easily deform to follow the shape of the buttocks.

The liquid-permeable top sheet 3 can be made of any material used as top sheet material for absorbent articles, such as sanitary napkins, diapers and incontinence protectors. It can for example be a nonwoven material, a perforated plastic film or a laminate of two or more layers. Preferably, the top sheet is made of hydrophobic material. In the embodiment described above, the top sheet is attached to the elastic bands 9,10 as well as the bottom of the hole but it is of course possible to attach the top sheet also to the upper absorbent layer. Such an attachment must be liquid permeable and can be made using liquid-permeable adhesive or a pattern of adhesive spots or strings.

The elastic band 9,10 and 13 can be made of different kinds of elastic material, for example an elastic foam, but can also consist of a strip of elastic material, such as a rubber band, a polyurethane strip, a strip of elastic nonwoven or several threads of elastic material laminated to one or two layers of non-elastic material, such as nonwovens. A suitable elastic band is an elastic foam from CALLIGEN FOAM Ltd, England, sold under the trade name Elastic Foam XD4100AS. In order to distribute the elastic force of the pre-tensioned bands 9,10 on a relatively large area of the upper absorbent layer while leaving the created bowls substantially uncovered, the width of each band should be 10-20% of the width of the article.

By elastic material is in the present application meant a material that recovers at least 10%, preferably at least 25% after elongation.

The upper absorbent layer 5 can consist of any known absorbent material used for absorbent articles, such as sanitary napkins, diapers and incontinence protectors. It can consist of cellulose fluff preferably mixed with super absorbent particles (SAP). One example of a suitable material for the upper absorbent layer is pulp mixed with about 25% of SAP from BASF, Ludwigshafen, Germany under the trade name B7160. The mixture of cellulose fluff and SAP has preferably a density of 0.085-0.125 g/cm$^3$.

The acquisition material 7 can consist of any material used as acquisition material for absorbent articles, such as sanitary napkins, diapers and incontinence protectors. It is an open material, which easily will pass received liquid to the underlying lower absorbent layer. Furthermore, it shall not collapse after receiving liquid but remain open. A suitable material for the acquisition layer is a hydrophobic wadding of nonwoven, through air available from Libeltex, Belgium having the trade name Dry Web T23W.

The lower absorbent layer 6 can consist of a material similar to the material in the upper absorbent layer. However, the capillaries in the lower absorbent layer should preferably be smaller than in the upper absorbent layer so that liquid temporarily stored in the acquisition layer will first be sucked up by the lower absorbent layer. Thereby most of the liquid emitted by a user of the article will be stored in the lower absorbent layer and only a small amount of liquid will be absorbed and stored in the upper absorbent layer. A suitable material for the lower absorbent layer is pulp mixed with about 35% SAP, of the same or a similar quality as for the upper absorbent layer.

Furthermore, SAP in the lower layer 6 have the main function of increasing the liquid storing capacity of this layer whereas the main function of possible SAP in the upper layer 5 is to prevent rewet of liquid absorbed in this layer if the article is compressed by external forces during use, for example when the user is cycling. The SAP in the upper absorbent layer will thus advantageously be of a different type than SAP used in the lower absorbent layer but can be of the same quality in a lower concentration.

The backing sheet can be made of any material used as backing sheet in absorbent articles, such as sanitary napkins, diapers and incontinence protectors. It can for example consist of a plastic film, a liquid-impermeable nonwoven material comprising one or more layers or a laminate of a plastic film and a nonwoven material. To advantage, a vapour permeable material can be used.

As stated above, the contractive forces of the pre-tensioned elastic bands 9,10 should be so strong that the angle α (see FIG. 6) will be greater than 30 degrees. The forces needed are thus dependent on the size of the article and the materials and thicknesses of the different layers in the absorbent core and can therefore not be easily defined. However, the angle α is well suited to define the pre-tensioned needed.

Furthermore, the absorbent core should have such a stiffness and strength that shape of the article described with reference to FIGS. 3-6 is obtained without local rupture or local disintegration in any of the layers making up the absorbent core. The upper and lower absorbent layers usually have the required strength and stiffness and do not create any problem in this respect. If there is a risk that local rupture or disintegration should occur, the integrity of the different layers can be ensured by inserting a stiffening element between the lower absorbent layer and the backing sheet. Such a stiffening element can consist of a plastic sheet with or without folding lines, a hydrophobic nonwoven material, a paper material with a hydrophobic surface, etc.

The Y-shape of the hole 8 can be varied in order to create the desired bowl-shape in the front and middle portions of the article by varying the angle between the diverging legs 8b,8c of the Y and by the varying the relative length of the different legs of the Y. Also the width of the legs can be varied. However, the outer angle between leg 8a and the respective legs 8b,8c should always be greater than 90 degrees.

As stated above, the legs of the hole 8 functions as folding lines for the absorbent core. Thereby the middle portion of the article in use being disposed between the thighs of the user can easily follow the movements of the thighs only by varying the angle of folding around the edge of the leg 8a without deformation of the absorbent core. The elastic bands 9,10 will bias the walls of the valley-shaped bowl in the middle portion of the article to the position shown in FIGS. 3-6 when then article is not subjected to external forces.

In FIGS. 7 and 8, a production line according to a preferred embodiment of the method of manufacturing absorbent articles is schematically disclosed.

A web 16 of backing sheet material is drawn from a storage roll 17 and laid on a conveyer. Thereafter, a row of absorbent cores a laid onto the web 16. The absorbent cores of the articles include lower absorbent layer 18 which is laid onto the web 16 with the aid of a transfer wheel 19, acquisition layer 20 which is laid onto the lower absorbent layers 18 with the aid of a transfer wheel 21 and upper absorbent layer 22 which is laid onto the acquisition layer 20 with the aid of a transfer wheel 23. In the method of the invention, the absorbent cores are laid into a row such as the front ends of the absorbent cores are turned against each other as well as the rear ends. Thus, in the row of absorbent cores laid onto the web 16, every second absorbent core is turned 180 degrees in relation to an adjacent absorbent core. As is evident from FIG. 1, the lower absorbent layer and the acquisition layer is not disposed symmetrically in a longitudinal direction in a manufactured article but have their main extension in the front part of the article. This means that the intervals between individual layers in the row of these layers laid onto the web 16 will differ, the distance between adjacent such layers being small in the front ends thereof and long in the rear ends thereof. In the present production line the layers are disposed on the respective transfer wheel so that they are laid at correct intervals onto the web 16. One way of ensuring correct placement and configuration of the different layers in the absorbent core is to construct moulds and the distances between moulds in respective mat-forming wheel so that the formed layers delivered to a transfer wheel has their front ends turned against each other and are disposed at the correct intervals in relation to each other. For the reason of simplicity, such mat-forming wheels are not shown in FIG. 1.

If the absorbent layer should have been laid onto the web of top sheet material instead of the web of backing sheet material the layers in the absorbent core would of course be laid in inverted order. The order of applying the layers of a multi-layered absorbent core can thus vary.

After, thus having laid a row of absorbent cores comprising the layers 18,20,22 with their front ends and rear ends turned against each other onto the web 16, a web 24 of top sheet material from a storage roll 25 is laid onto the web 16 and the row of absorbent cores placed thereon. Before the web 24 of top sheet material is brought together with web 16, rows of pre-tensioned elastic bands are attached to web 24. This can advantageously be accomplished by pressing elastic bands 26-28 from a roller 29, schematically shown in FIG. 9, onto the web 24. The roller 29 takes bands from a storage roller 30 on which the bands are wound up, tensions the bands and hold the tensioned bands by sub-pressure during the transfer from the storage roller 30 to the top sheet web 24. Thereby, one row of centrally disposed pre-tensioned elastic bands 28 and two rows of pre-tensioned elastic bands 26,27 which are placed laterally equidistant from the centre line of the web 24, are attached thereto. The lateral placement of the bands 26,27 is such that these bands will be located over the lateral edge portions of the absorbent core in the front part of the produced articles. The laying-out device does also include a cutting device (not shown) for cutting the bands from the storage roller when the desired length of elongated bands are held by the roller 29. A device 31 for applying adhesive to the bands 26-28 is also shown in FIG. 7. However, such a device can instead apply strings of adhesive to the web 24 before the bands 26-28 are pressed against this web.

The web 24 passes a device 32 for applying adhesive to the underside of the bands 26-28, i.e. the side being opposite to the side thereof being attached to the web 24, before it is brought together with the web 16 and the row of absorbent cores laid thereupon. In the described embodiment the device 32 applies adhesive also to the web 24 of top sheet material in addition to the undersides of the bands 26-28.

The composite webs 16,24 with the absorbent cores disposed therebetween then passes through a compressing device 33 in which the web 24 is pressed against the upper side of the absorbent cores and the webs 16,24 are pressed against each other in the areas outside the absorbent cores. Moreover, the web 24 of top sheet material is pressed into the Y-shaped holes in the upper layer 22 of the absorbent cores so that the top sheet in the manufactured articles is attached to the bottom of these holes. In order to accomplish this, the upper roller of the compressing device 33 is profiled in a suitable way.

Figure 10:
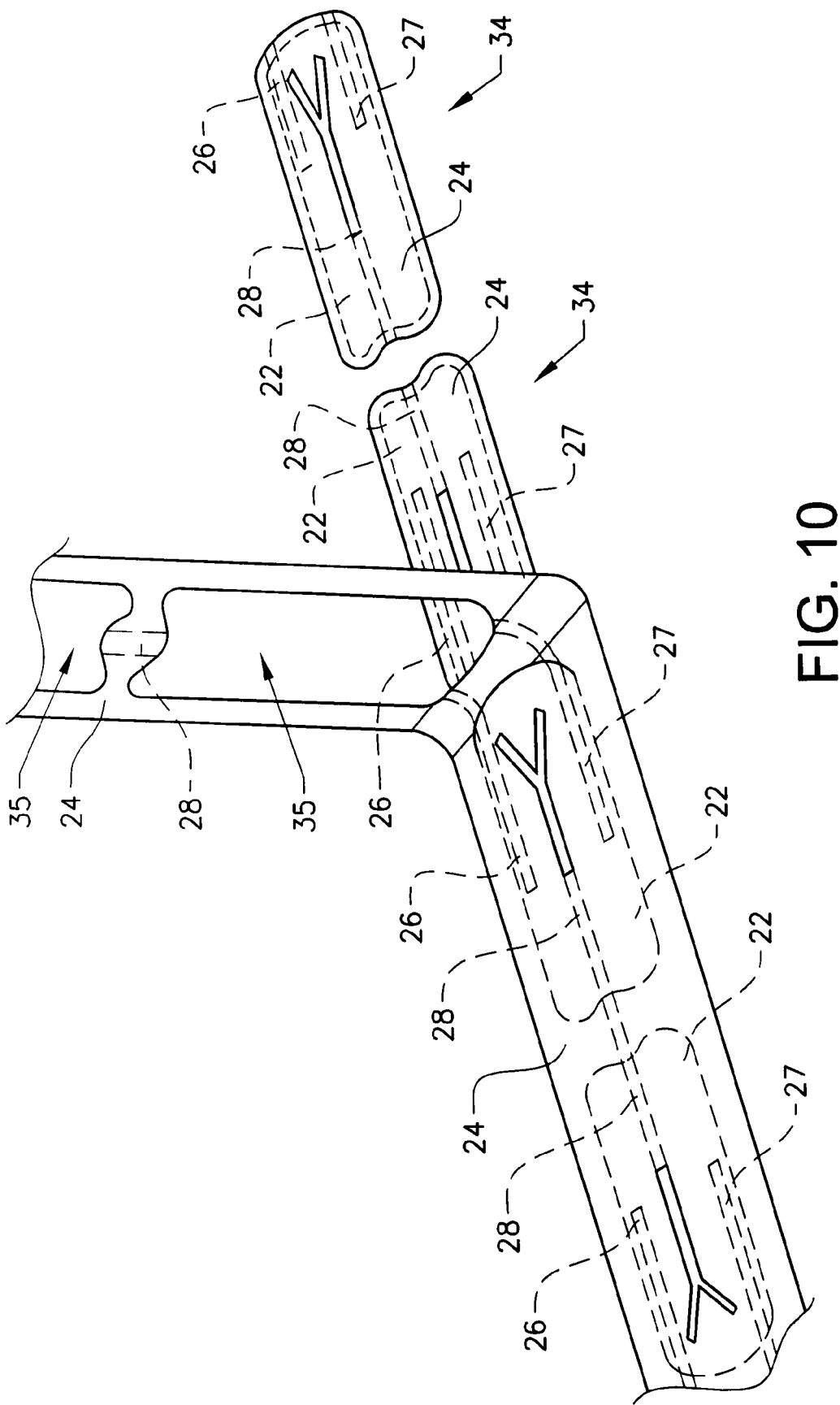

After the webs 16,24 have passed the compressing device 33, a web of connected article blanks is formed. Individual absorbent articles 34 are then cut out of the web of connected article blanks by a cutting device 35, cutting out the profile of each individual article. At least one of the webs 16,24 and preferably both of the webs are so wide that after the cutting out of the profiles of individual articles, the waste material will form a continuous web of waste material, as indicated in FIG. 9 and schematically shown in FIG. 10 in which there also is a distance between the articles cut out from the web of connected article blanks. The web of waste material will thus contain remaining parts of webs 16,24 and parts of elastic bands 26-28 remaining between the webs 16, 24 in the parts thereof located between the row of holes 35 having the contour of the cut out articles 34.

After manufacture, the absorbent articles are packaged. The packaging can include folding first the rear third of the article onto the middle portion and thereafter folding the front third portion over the in-folded rear portion.

The components in the production line described with reference to FIGS. 7-9 are all per se known to a skilled man and need not be further described.

The method has been described for producing disposable incontinence protectors for light incontinent females but can of course also be used for other types of disposable absorbent articles, such as diapers, sanitary napkins and the like. If the method is used for articles intended to be attached to the inside of underpants an adhesive coating and a layer of release material covering the coating is applied to the underside of the web 16 of backing sheet material, preferably just before the web of connected article blanks reach the cutting device.

The described embodiment can of course be modified in several respects without leaving the scope of invention. For example, the lower absorbent layer can have the same shape as the upper absorbent layer and the acquisition layer can have a greater extension. The elastic band 13,28 in the rear portion of the article can be deleted. The pre-tension in the band can be varied so that the pre-tension in the rear elastic band 13,28 is lower or higher than in the bands 9,10,26,27. The adhesive layer 11 need not be homogenous but can consist of several strings of adhesive or a pattern of adhesive. It is also possible to substitute this adhesive layer by a frictional material or hooks type material, The elastic bands need not to be liquid-permeable, even if this is preferred, and thus need the adhesive used to attach these bands to the top sheet and the upper absorbent layer not be liquid-permeable, even if this is preferred. If thermoplastic fibres are present in the upper absorbent layer, the attachment of this layer to the elastic bands can be made by welding with the aid of an ultra-sonic welding device or other heat-sealing devices. The shape of the article can also differ. The different layers in the absorbent cores can be brought together before they are delivered to the web of backing sheet material. The absorbent cores can be laid upon the web of top sheet material instead of the web of backing sheet material, in which case the rows of elastic bands are attached to the web of top sheet material before the absorbent cores are laid thereupon. The components in the production line can have other construction than the described components, for example can the different absorbent layers be delivered directly from mat-forming wheels. The scope of protection should therefore not be limited by the described embodiments but be defined by the enclosed patent claims.

The invention claimed is:

1. A method of manufacturing absorbent articles having an absorbent core enclosed between casing sheets and having continuous elastic elements located in a front part, a rear part, or both front and rear parts of the article, comprising the steps of laying a row of absorbent cores on a first web of casing material running in a machine direction with the longitudinal direction of the cores being extended in the machine direction, applying a second web of casing material onto the web containing the row of absorbent cores, applying the elastic elements to one of said webs before it contacts said row of absorbent cores, thereby forming a row of connected absorbent article blanks, and thereafter cutting individual absorbent articles out of the row of article blanks, wherein the absorbent cores are laid onto the first web front part to front part and rear part to rear part, and at least one of the continuous elastic elements are applied over two subsequent absorbent cores with a length in the longitudinal direction corresponding to twice the length of a respective continuous elastic element in the front and/or rear part of the article, wherein two of the elastic elements are applied to one of said webs in positions corresponding to opposite lateral sides of the front part of each absorbent core, and the lateral sides being substantially parallel to each other.

2. The method according to claim 1, wherein said first web of casing material is a web of backing sheet material and said elastic elements are applied to the second web of casing material, said second web of casing material is a web of top sheet material.

3. The method according to claim 1, wherein said second web of casing material is a web of backing sheet material and said elastic elements are applied to the first web of casing material, said first web of casing material is a web of top sheet material.

4. The method according to claim 1, wherein one of the elastic elements is applied to the web of top sheet material in a position corresponding to the rear part of each absorbent core and is extended along the longitudinal axis of said web.

5. The method according to claim 1, wherein each elastic element has a straight extension.

6. The method according to claim 1, wherein the elastic elements are attached to lateral side portions of the absorbent cores.

7. A method of manufacturing absorbent articles having an absorbent core enclosed between casing sheets and having continous elastic elements located in a front part, a rear part, or both front and rear parts of the article, comprising laying a row of absorbent cores on a first web of casing material running in a machine direction with the longitudinal direction of the cores being extended in the machine direction, applying a second web of casing material onto the web containing the row of absorbent cores, applying the elastic elements to one of said webs before it contacts said row of absorbent cores, thereby forming a row of connected absorbent article blanks, and thereafter cutting individual absorbent articles out of the row of article blanks, wherein the absorbent cores are laid onto the first web front part to front part and rear part to rear part, and at least one of the continuous elastic elements are applied over two subsequent absorbent cores with a length in the longitudinal direction corresponding to twice the length of a respective continuous elastic element in the front and/or rear part of the article, wherein two of the continuous elastic elements are applied to one of said webs in positions corresponding to opposite lateral sides of the front part of each absorbent core, and wherein the continuous elastic members are substantially parallel to a direction of movement of the web.

8. An absorbent article manufactured by the method according to claim 7 and having an absorbent core enclosed between casing sheets and elastic elements located in a front part, a rear part, or both front and rear parts of the article, wherein the elastic elements in the front part of the article extend to the limit of the front end of the article and are attached to opposite lateral sides of the absorbent core.

9. The method according to claim 1, wherein the at least one of the continuous elastic elements are applied over two subsequent absorbent cores with a length in the longitudinal direction corresponding to twice the length of a respective continuous elastic element in the front and/or rear part of the article and a distance between adjacent article blanks in the row of article blanks.

10. The method according to claim 7 wherein the at least one of the continuous elastic elements are applied over two subsequent absorbent cores with a length in the longitudinal direction corresponding to twice the length of a respective continuous elastic element in the front and/or rear part of the article and a distance between adjacent article blanks in the row of article blanks.

* * * * *